United States Patent
Yu et al.

(10) Patent No.: US 10,048,267 B2
(45) Date of Patent: Aug. 14, 2018

(54) METHODS AND COMPOSITIONS FOR ASSAYING BLOOD LEVELS OF LEGUMAIN

(71) Applicants: Xiaohong Yu, San Diego, CA (US); Fang Guo, Shanghai (CN)

(72) Inventors: Xiaohong Yu, San Diego, CA (US); Fang Guo, Shanghai (CN)

(73) Assignee: NINGBO ZIYUAN MEDICAL DEVICES INC., Ningbo (CN)

( * ) Notice: Subject to any disclaimer, the term of this patent is extended or adjusted under 35 U.S.C. 154(b) by 0 days.

(21) Appl. No.: 14/928,353

(22) Filed: Oct. 30, 2015

(65) Prior Publication Data

US 2017/0089910 A1    Mar. 30, 2017

(30) Foreign Application Priority Data

Sep. 30, 2015   (CN) .......................... 2015 1 0641455

(51) Int. Cl.
  *G01N 33/53*   (2006.01)
  *G01N 33/574*  (2006.01)
(52) U.S. Cl.
  CPC .......... *G01N 33/57496* (2013.01); *G01N 2333/96466* (2013.01)
(58) Field of Classification Search
  None
  See application file for complete search history.

(56) References Cited

U.S. PATENT DOCUMENTS

2002/0137904 A1*  9/2002  Billing-Medel ....... C07K 14/47
                                                      536/23.1
2006/0135410 A1*  6/2006  Liu ................ A61K 47/48361
                                                      514/1.3

FOREIGN PATENT DOCUMENTS

WO    2007083100 A2    7/2007

OTHER PUBLICATIONS

R&D Legumain ELISA kit, R&D, DY4769, 2012.*
Choi et al, JBC, 274:27747-53, 1999.*
Angeloni, Stephen, et al., "xMAP Cookbook: A collection of methods and protocols for developing multiplex assays with xMAP Technology", Luminex Corp, Jul. 1, 2013, p. 6 In 1-4, p. 38, p. 43 Figure, p. 43 Summary of Protocol, p. 44 Table row 1, p. 44 Table row 2, p. 44-46 Protocol 4.1.1., p. 45 In 1-5, p. 46 In 10, p. 112 Table row 7.
Invitrogen, "Dynabeads Pan Mouse IgG", Life Technologies Corp. (May 2012) <retrieved from 11 https://tools.thermofisher.com/contenUsfs/manuals/dynabeads_pan_mouse_IgG_man.pdf on Dec. 2, 2016> p. 1 col. 1 Product Description, p. 2 col. 1 Isolate Cells—Direct Technique.
Invitrogen, "Dynabeads M-450 Tosylactivated", Life Technologies Corp. (Jun. 2012) <retrieved from https://tools.thermofisher.com/contenUsfs/manuals/dynabeads_m450tosylactivated_man.pdf on Dec. 2, 2016> p. 1 col. 1 Product Description, p. 1 col. 3 Prepare Sample, p. 2 col. 1-2 Isolate Cells.
Liu et al., "Overexpression of Legumain in Tumors Is Significant for Invasion/Metastasis and a Candidate Enzymatic Target for Prodrug Therapy", Cancer Res., vol. 63, No. 11, Jun. 1, 2003, pp. 2957-2964.
Young, Lee, W., "International Search Report and Written Opinion", Patent Cooperation Treaty Application No. PCT/US2016/05458, Untied States Patent Office as Search Authority, dated Dec. 29, 2016, 10 pages.

* cited by examiner

*Primary Examiner* — Lei Yao
(74) *Attorney, Agent, or Firm* — Greer, Burns & Crain, Ltd.; Gregory P. Einhorn (57) ABSTRACT

In one aspect, a homogenous assay method for determination of blood levels of legumain molecules (an asparaginyl endopeptidase) is disclosed. In one aspect, the assay utilizes specific sizes of nanoparticles that are coated with antibody or antibodies specifically towards legumain molecule or its fragment(s). In one aspect, the assay is designed in a homogenous manner with a dynamic range from 0.2 to 160 ng/mL. In another aspect, disclosed herein is a kit for assaying blood levels of legumain comprising two parts of reagents (R1 and R2), which kit is adaptable to be used on clinical chemistry analyzers. In one aspect, the cut-off values for differentiating normal from high risk of cancers such as breast cancer, colorectal cancer and stomach cancer are 18±3 ng/mL.

16 Claims, 7 Drawing Sheets

METHODS AND COMPOSITIONS FOR ASSAYING BLOOD LEVELS OF LEGUMAIN

RELATED APPLICATIONS

This U.S. utility patent application claims benefit of priority under 35 U.S.C. § 119(a) of China patent application no. 201510641455.6, filed Sep. 30, 2015. The aforementioned application is expressly incorporated herein by reference in its entirety and for all purposes.

TECHNICAL FIELD

In certain aspects, the present disclosure relates to methods, kits, and devices for analyzing biomolecules. In particular aspects, the present disclosure relates to methods, kits, and devices for determining legumain concentrations in a sample. In some embodiments, legumain concentrations are determined in blood samples based on a microparticle enhanced immunoassay, such as a latex agglutination immunoassay.

BACKGROUND

Legumain is a protein that in human is encoded by the LGMN gene (Chen J. M. et al., J. Biol. Chem. 1997; Tanaka T. et al., Cytogenet. Cell Genet. 1966; Halfon S. et al., FEBS Lett. 1998). This gene encodes a cysteine proteinase that has a strict specificity for hydrolysis of asparaginyl bonds, cleaving peptide bonds with Asn or Asp at the P1 position (Schwarz G. et al., J. Biol. Chem. 2002). Several alternatively spliced transcript variants have been described, but the biological validity of only two have been determined. These two variants encode the same isoform (Yamane T. et al., Biochem. Biophys. Res. Commun. 2013). Legumain is over expressed in colorectal cancer, ovarian cancer, breast cancer and other types of cancers (Liu C. et al., Cancer Res. 2003; Murthy R. V. et al., Clin. Cancer Res. 2005). Legumain was identified as a tumor biomarker from gene expression profiling and tumor tissue array (Guo P. et al., PLoS One, 2013). Mammalian legumain is involved in the processing of bacterial peptides and endogenous proteins for MHC class II presentation in the lysosomal/endsommal systems. Legumain has been observed to be a potential predictive biomarker for several types of cancers (Wu M. et al., Asian Pac. J. Cancer Prev. 2014; Gawenda J. et al., Breast Cancer Res. Treat. 2007). It was demonstrated in membrane-associated vesicles concentrated at the invadopodia of tumor cells and on cell surfaces where it co-localized with integrins (Liu Y., Mol. Pharm. 2012). Overexpression of legumain may be associated with the formation of solid tumors (Liu et al., Cancer Res. 2003). Cells overexpressing legumain can possess increased migratory and invasive activity in vitro and adopt an invasive and metastatic phenotype in vivo, inferring the significance of legumain in tumor invasion and metastasis (Lin Y. et al., J. Nat. Cancer Inst. 2014). It has also been demonstrated that legumain promotes cell migration, and overexpression is associated with enhanced tissue invasion and metastasis (Haugen et al., Eur. J. Cancer 2015). The unique functional properties of legumain and its high-level expression in many human tumors support that it is a potential candidate as enzymatic target for prodrug activation and tumor eradicative therapy (Cheng Liu et al., Cancer Res. 2003). A prodrug strategy incorporating a legumain cleavable peptide substrate onto doxorubicin was developed (Liu et al., Nat Commun. 2014; Stern et al., Bioconjug. Chem. 2009).

Despite that legumain is attractive as a target for anticancer drug design and the progress of pharmaceutical research on this target, there is a lack of clinical diagnostic method for determination of blood levels of legumain in an automated fashion by clinical chemistry analyzers or automated immunoanalyzers. Therefore, it is desired to develop a fully automated legumain test that is adaptable to clinical chemistry analyzers or immunoanalyzers in clinical settings.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In some aspects, provided herein is a highly sensitive and homogeneous assay specific for human legumain in blood, which allows clinicians, for the first time, to test legumain levels in blood samples using fully automated chemistry analyzers which are the most commonly available analyzers in clinic laboratories. In some aspects, the high sensitivity of the assay is reached through specific improvements of conventional latex agglutination immunoassay in the area of latex particle size selection, antibody coupling ratio, use of specific type and/or amount of agglutination enhancers, and/or conditions of heat stress treatment at proper temperature and/or duration. In some aspects, the assay is rapid with the total reaction time of less than about 40 minutes, less than about 30 minutes, less than about 20 minutes, less than about 10 minutes, or less than about 5 minutes. In some aspects, the present disclosure relates to a method for overcoming low sensitivity and high non-specificity of latex agglutination immunoassay for legumain in blood samples. In some aspects, with this sensitive and specific assay, for the first time, the circulating legumain molecules in serum or plasma samples are measured using fully automated chemistry analyzers. In some aspects, using a method disclosed herein, the serum levels of legumain in samples from breast cancer, colorectal cancer and stomach cancer patients are significantly elevated in comparison with the levels of legumain in the samples from healthy volunteers. In some aspects, for the first time, the clinical cut-off values that can be used by clinicians to assess the risks of cancers are established, especially for solid tumors such as breast cancer, colorectal cancer and stomach cancer which often have their circulating legumain levels in blood significantly above the cut-off values.

In one aspect, disclosed herein is a method for determining the level of legumain in a sample, comprising: 1) contacting a sample containing or suspected of containing legumain with a microparticle coated with an antibody or fragment thereof that specifically binds legumain or a degradation fragment thereof; 2) detecting the optical or signal change of the sample contacted with the microparticle; and 3) determining the level of legumain in the sample by comparing the optical or signal change with a calibrator of a known level of legumain. In some embodiments, the sample is a biological sample. In some embodiments, the biological sample is a blood, serum, or plasma sample. In any of the preceding embodiments, the microparticle can comprise a plurality of microparticles.

In any of the preceding embodiments, the method can further comprise: 4) comparing the level of legumain in the sample with a normal reference range or cut-off value, wherein the sample is from a subject having or suspected of having cancer, and the level of legumain in the sample being outside the normal reference range or above the cut-off value indicates a higher risk of cancer in the subject.

In any of the preceding embodiments, the legumain can be of mammalian origin. In any of the preceding embodiments, the legumain can be of human origin. In any of the preceding embodiments, the legumain can be an asparaginyl endopeptidase [EC 3.4.22. 34] or can have an asparaginyl endopeptidase [EC 3.4.22. 34] activity.

In any of the preceding embodiments, the antibody can be a monoclonal or polyclonal antibody. In any of the preceding embodiments, the antibody can be specific for a mammalian legumain, a human legumain, or a proteolytic degradation fragment thereof. In any of the preceding embodiments, the antibody fragment can be an Fab, F(ab')2, Fv, or scFv. In any of the preceding embodiments, the antibody can be a fully human antibody. In any of the preceding embodiments, the antibody or fragment thereof can be recombinantly produced.

In any of the preceding embodiments, the antibody or fragment thereof and/or the microparticle can be coupled to an agent. In one aspect, the agent is an agent for detection. In one aspect, the agent for detection is for chemiluminescence or fluorescence detection.

In any of the preceding embodiments, the microparticle can be a latex particle, a gold particle, or a magnetic particle. In any of the preceding embodiments, the microparticle can have a diameter ranging from about 5 nm to about 2000 nm. In particular embodiments, the diameter can range from about 5 nm to about 10 nm, about 10 nm to about 20 nm, about 20 nm to about 40 nm, about 40 nm to about 80 nm, about 80 nm to about 100 nm, about 100 nm to about 120 nm, about 120 nm to about 140 nm, about 140 nm to about 160 nm, about 160 nm to about 180 nm, about 180 nm to about 200 nm, about 200 nm to about 220 nm, about 220 nm to about 240 nm, about 240 nm to about 260 nm, about 260 nm to about 280 nm, about 280 nm to about 300 nm, about 300 nm to about 320 nm, about 320 nm to about 340 nm, about 340 nm to about 360 nm, about 360 nm to about 380 nm, about 380 nm to about 400 nm, about 400 nm to about 500 nm, about 500 nm to about 600 nm, about 600 nm to about 700 nm, about 700 nm to about 800 nm, about 800 nm to about 900 nm, about 900 nm to about 1000 nm, about 1000 nm to about 1100 nm, about 1100 nm to about 1200 nm, about 1200 nm to about 1300 nm, about 1300 nm to about 1400 nm, about 1400 nm to about 1500 nm, about 1500 nm to about 1600 nm, about 1600 nm to about 1700 nm, about 1700 nm to about 1800 nm, about 1800 nm to about 1900 nm, or about 1900 nm to about 2000 nm. In any of the preceding embodiments, the microparticle can have a diameter ranging from about 40 nm to about 400 nm.

In any of the preceding embodiments, the microparticle can be a magnetic particle, and the method can further comprise one or more washing steps. In any of the preceding embodiments, the detecting step can further comprise detecting chemiluminescence and/or fluorescence.

In any of the preceding embodiments, the ratio of the antibody or fragment thereof to the available coating sites on the microparticle can be between about 0.1 and about 1.0. In specific embodiments, the ratio can be between about 0.1 and about 0.2, between about 0.2 and about 0.3, between about 0.3 and about 0.4, between about 0.4 and about 0.5, between about 0.5 and about 0.6, between about 0.6 and about 0.7, between about 0.7 and about 0.8, between about 0.8 and about 0.9, or between about 0.9 and about 1.0. In any of the preceding embodiments, the ratio of the antibody or fragment thereof to the available coating sites on the microparticle can be between about 0.5 and about 1.0.

In any of the preceding embodiments, an agglutination enhancer or stimulant can be used in the contacting step. In one aspect, the agglutination enhancer or stimulant is polyethylene glycol. In one aspect, the molecular weight of the polyethylene glycol ranges from about 600 Da to about 100,000 Da. In specific embodiments, the molecular weight of the polyethylene glycol can range from about 600 to about 1,000, about 1,000 to about 2,000, about 2,000 to about 3,000, about 3,000 to about 4,000, about 4,000 to about 5,000, about 5,000 to about 10,000, about 10,000 to about 20,000, about 20,000 to about 30,000, about 30,000 to about 40,000, about 40,000 to about 50,000, about 50,000 to about 60,000, about 60,000 to about 70,000, about 70,000 to about 80,000, about 80,000 to about 90,000, or about 90,000 to about 100,000 Da. In any of the preceding embodiments, the final concentration of the polyethylene glycol can range from about 0.3 to about 1.5% (w/v). In specific embodiments, the concentration of the polyethylene glycol can range from about 0.3 to about 0.4, about 0.4 to about 0.5, about 0.5 to about 0.6, about 0.6 to about 0.7, about 0.7 to about 0.8, about 0.8 to about 0.9, about 0.9 to about 1.0, about 1.0 to about 1.1, about 1.1 to about 1.2, about 1.2 to about 1.3, about 1.3 to about 1.4, about 1.4 to about 1.5% (w/v).

In another aspect, the agglutination enhancer or stimulant is polyvinyl pyrrolidone. In one aspect, the molecular weight of the polyvinyl pyrrolidone ranges from about 10,000 Da to about 750,000 Da. In specific embodiments, the molecular weight of the polyvinyl pyrrolidone can range from about 10,000 to about 20,000, about 20,000 to about 40,000, about 40,000 to about 80,000, about 80,000 to about 160,000, about 160,000 to about 320,000, about 320,000 to about 640,000, or about 640,000 to about 750,000 Da. In any of the preceding embodiments, the final concentration of the polyvinyl pyrrolidone can range from about 0.1 to about 3.0% (w/v). In specific embodiments, the concentration of the polyvinyl pyrrolidone can range from about 0.1 to about 0.2, about 0.2 to about 0.3, about 0.3 to about 0.4, about 0.4 to about 0.5, about 0.5 to about 0.6, about 0.6 to about 0.7, about 0.7 to about 0.8, about 0.8 to about 0.9, about 0.9 to about 1.0, about 1.0 to about 1.1, about 1.1 to about 1.2, about 1.2 to about 1.3, about 1.3 to about 1.4, about 1.4 to about 1.5, about 1.5 to about 1.6, about 1.6 to about 1.7, about 1.7 to about 1.8, about 1.8 to about 1.9, about 1.9 to about 2.0, about 2.0 to about 2.1, about 2.1 to about 2.2, about 2.2 to about 2.3, about 2.3 to about 2.4, about 2.4 to about 2.5, about 2.5 to about 2.6, about 2.6 to about 2.7, about 2.7 to about 2.8, about 2.8 to about 2.9, or about 2.9 to about 3.0% (w/v).

In any of the preceding embodiments, the microparticle coated with the antibody or fragment thereof can be heat stressed for at least about 10 hours at a temperature between about 30° C. and about 50° C. In specific embodiments, the time for heat stress is about 10, 11, 12, 13, 14, 15, 16, 17, 18, 19, 20, 21, 22, 23, 24, 25, 26, 27, 28, 29, 30, 31, 32, 33, 34, 35 hours, or about 3, 4, 5, 6, 7, 8, 9, or 10 days. In specific embodiments, the temperature for heat stress is between about 30 and about 35, between about 35 and about 40, between about 40 and about 45, or between about 45 and about 50° C. In any of the preceding embodiments, the microparticle coated with the antibody or fragment thereof can be heat stressed at about 45° C. for between about one day and about five days.

In any of the preceding embodiments, the sample can be a serum or plasma sample from a human, or a non-human mammal.

In any of the preceding embodiments, the cancer can be a solid tumor. In one aspect, the cancer is selected from the group consisting of breast cancer, ovarian cancer, colorectal cancer, stomach cancer, and lung cancer.

In another aspect, disclosed herein is a kit for determining the level of legumain in a sample, comprising: a first reagent (R1) comprising a buffer with its pH value ranging from about 3.0 to about 10.0; and a second reagent (R2) comprising a microparticle coated with an antibody or fragment thereof that specifically binds legumain or a degradation fragment thereof. In particular embodiments, the pH of R1 ranges from about 3.0 to about 4.0, about 4.0 to about 5.0, about 5.0 to about 6.0, about 6.0 to about 7.0, about 7.0 to about 8.0, about 8.0 to about 9.0, or about 9.0 to about 10.0.

In any of the preceding embodiments, the microparticle can comprise a plurality of microparticles. In any of the preceding embodiments, the antibody can be a monoclonal or polyclonal antibody. In any of the preceding embodiments, the antibody can be specific for a mammalian legumain, a human legumain, or a proteolytic degradation fragment thereof. In any of the preceding embodiments, the antibody fragment can be an Fab, F(ab')2, Fv, or scFv. In any of the preceding embodiments, the antibody can be a fully human antibody. In any of the preceding embodiments, the antibody or fragment thereof can be recombinantly produced. In any of the preceding embodiments, the antibody or fragment thereof and/or the microparticle can be coupled to an agent. In one aspect, the agent is an agent for detection. In another aspect, the agent for detection is for chemiluminescence or fluorescence detection.

In any of the preceding embodiments, the microparticle can be a latex particle, a gold particle, or a magnetic particle. In any of the preceding embodiments, the microparticle can have a diameter ranging from about 5 nm to about 2000 nm. In any of the preceding embodiments, the microparticle can have a diameter ranging from about 40 nm to about 400 nm.

In any of the preceding embodiments, the microparticle can be a magnetic particle. In any of the preceding embodiments, the kit can further comprise a washing buffer.

In any of the preceding embodiments, the kit can further comprise one or more reagents for detecting chemiluminescence and/or fluorescence.

In any of the preceding embodiments, the ratio of the antibody or fragment thereof to the available coating sites on the microparticle can be between about 0.1 and about 1.0. In any of the preceding embodiments, the ratio of the antibody or fragment thereof to the available coating sites on the microparticle can be between about 0.5 and about 1.0.

In any of the preceding embodiments, the kit can further comprise an agglutination enhancer or stimulant. In any of the preceding embodiments, the agglutination enhancer or stimulant can be polyethylene glycol. In one aspect, the molecular weight of the polyethylene glycol in R2 ranges from about 600 Da to about 100,000 Da. In any of the preceding embodiments, the final concentration of the polyethylene glycol in R2 can range from about 0.3 to about 1.5% (w/v). In one aspect, the agglutination enhancer or stimulant is polyvinyl pyrrolidone. In another aspect, the molecular weight of the polyvinyl pyrrolidone in R2 ranges from about 10,000 Da to about 750,000 Da. In any of the preceding embodiments, the final concentration of the polyvinyl pyrrolidone in R2 can range from about 0.1 to about 3.0% (w/v).

In any of the preceding embodiments, the microparticle coated with the antibody or fragment thereof can be heat stressed for at least about 10 hours at a temperature between about 30° C. and about 50° C. In any of the preceding embodiments, the microparticle coated with the antibody or fragment thereof can be heat stressed at about 45° C. for between about one day and about five days.

In any of the preceding embodiments, the legumain can be of mammalian origin or of human origin. In any of the preceding embodiments, the legumain can be an asparaginyl endopeptidase [EC 3.4.22. 34] or have an asparaginyl endopeptidase [EC 3.4.22. 34] activity.

In any of the preceding embodiments, the kit can further comprise a calibrator or a calibrator set, packaged with R1 and/or R2, or separately.

In any of the preceding embodiments, the sample can be first mixed with a first reagent, followed by addition of a second reagent comprising the microparticle coated with the antibody or fragment thereof that specifically binds legumain or a degradation fragment thereof. In one aspect, the first reagent comprises a buffer. In some embodiments, the buffer has a pH value ranging from about 3.0 to about 10.0. In any of the preceding embodiments, the first reagent can comprise an agglutination enhancer or stimulant.

In any of the preceding embodiments, the risk of cancer can be assessed using an established cut-off value. In one aspect, the risk of cancer is assessed using an established cut-off value of 18.5±3 ng/mL of legumain level. In another aspect, the established cut-off value is for breast cancer, stomach cancer, and/or colorectal cancer.

In one aspect, the cut-off value for breast cancer, ovarian cancer, colon cancer, lung cancer, and/or stomach cancer is 18.5 ng/mL of legumain in a plasma or serum sample. In another aspect, the established cut-off value is set according to a sample condition, whether the sample is from a female or a male subject, and/or the type of cancer. In some embodiments, the established cut-off value is set between about 15.0 ng/mL and about 25.0 ng/mL. In particular embodiments, the cut-off value is set between about 15.0 and about 16.0, about 16.0 and about 17.0, about 17.0 and about 18.0, about 18.0 and about 19.0, about 19.0 and about 20.0, about 20.0 and about 21.0, about 21.0 and about 22.0, about 22.0 and about 23.0, about 23.0 and about 24.0, or about 24.0 and about 25.0 ng/mL.

In some embodiments, the established cut-off value is about 18.5 ng/mL of legumain in a plasma or serum sample for breast cancer and/or ovarian cancer. In other embodiments, the established cut-off value is between about 10 ng/mL and about 30 ng/mL for stomach cancer, colon cancer, and/or lung cancer.

DETAILED DESCRIPTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell, all of which are herein incorporated in their entireties by reference for all purposes.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

As used herein and in the appended claims, the singular forms "a," "an," and "the" include plural referents unless the context clearly dictates otherwise. For example, "a" or "an" means "at least one" or "one or more." Thus, reference to "a reagent" refers to one or more reagents, and reference to "the method" includes reference to equivalent steps and methods disclosed herein and/or known to those skilled in the art, and so forth.

As used herein, "legumain" includes the enzyme or enzyme fragments encoded by human LGMN gene. The enzyme has an EC number of [3.4.22.34].

As used herein, "antibody" includes not only intact polyclonal or monoclonal antibodies, but also fragments thereof (such as Fab, Fab', F(ab')2, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class.

As used herein, "latex particles" includes polystyrene beads with diameters ranging from 40 to 500 nm. The latex particles include polystyrene beads that are carboxylated or aminated. The density of the latex particles, without limitation, will vary generally between about 0.1 mg/mL and about 0.1 g/mL. Most latexes are composed of particles that are roughly microspherical, having diameters, without limitation, that vary between about 0.04 and about 1.0 microns. Most latexes are composed of particles having a net negative surface charge at neutral pH. The charge repulsion between the negative surface charges on the latex is important in maintaining the particles in suspension. As used herein, the term latex is intended to mean the property of suspension of discrete microparticles in an aqueous liquid.

As used herein the term "assessing" is intended to include quantitative and qualitative determination in the sense of obtaining an absolute value for the amount or concentration of the analyte present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein the term "sample" includes anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). As used herein, a "sample" can be a solution, a suspension, liquid, powder, a paste, aqueous, non-aqueous or any combination thereof. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, "blood sample" includes a whole blood sample or a plasma or serum fraction derived therefrom. Preferably, the blood sample refers to a human blood sample such as whole blood or a plasma or serum fraction derived therefrom. Also preferably, the blood sample is pre-treated before the assay by removing substantially all hemoglobin (i.e., red blood cells) in order to eliminate or significantly reduce the oxidative interference from the hemoglobin molecules.

As used herein the term "whole blood" includes a blood sample that has not been fractionated and contains both cellular and fluid components. As used herein, "whole blood" refers to freshly drawn blood which is tested before it clots, or a conventionally-drawn blood sample, which may be drawn into a vacutainer, and which may contain an anticoagulant, such as lithium-heparin, EDTA etc., or to which one or more other standard clinical agents may be added in the course of routine clinical testing.

As used herein, the term "plasma" includes the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" includes whole mammalian serum, such as whole human serum. Further, as used herein, "serum" refers to blood plasma from which clotting factors (e.g., fibrinogen) have been removed.

As used herein, the term "fluid" includes any composition that can flow. Fluids thus encompass compositions that are in the form of semi-solids, pastes, solutions, aqueous mixtures, gels, lotions, creams and other such compositions.

As used herein, the term "disease" or "disorder" includes a pathological condition in an organism resulting from, e.g., infection or genetic defect, and characterized by identifiable symptoms.

As used herein, "contacting" means bringing two or more components together. "Contacting" can be achieved by mixing all the components in a fluid or semi-fluid mixture. "Contacting" can also be achieved when one or more components are brought into contact with one or more other components on a solid surface such as a solid tissue section or a substrate.

As used herein, the term "comparing" generally means examining in order to note similarities or differences between two or more values. Preferably, "comparing" refers to quantitative comparisons such as, for example, subtracting one value from another, calculating a ratio of two values, calculating a percentage of one value with respect to another, or combining these types of calculations to produce a single number. As used herein, "comparing" further refers to comparisons made by a human, comparisons made by a computer or other processor, and comparisons made by a human in combination with a computer or other processor.

It is understood that aspects and embodiments as provided herein include "consisting" and/or "consisting essentially of" aspects and embodiments.

The term "binding" is used herein to refer to an attractive interaction between two molecules which results in a stable association in which the molecules are in close proximity to each other. Molecular binding can be classified into the following types: non-covalent, reversible covalent and irreversible covalent. Molecules that can participate in molecular binding include polypeptides, polynucleotides, carbohydrates, lipids, and small organic molecules such as pharmaceutical compounds. Polypeptides that form stable complexes with other molecules are often referred to as receptors while their binding partners are called ligands. Polynucleotides can also form stable complex with themselves or others, for example, DNA-protein complex, DNA-DNA complex, DNA-RNA complex.

Other objects, advantages and features of the present disclosure will become apparent from the following specification taken in conjunction with the accompanying drawings.

Latex agglutination immunoassay is based on the formation of detectable agglutination by binding between a multivalent latex antibody reagent and a corresponding multivalent form of the antigen. Latex agglutination immunoassay is a homogenous assay that can be used with general clinical chemistry analyzers commonly available in clinical laboratories. Though latex agglutination immunoassay is commonly used in clinical diagnostics, the method is not as sensitive as heterogeneous assay such as magnetic particle based chemiluminescent immunoassay. The conventional latex agglutination immunoassay is mostly suitable for determining analytes (proteins) at concentrations above 1.0 ng/mL in blood samples. However, the blood concentration of legumain in normal subjects is between 0.3 and 5.0 ng/mL, and the detection sensitivity requirement for low end is below the detection limit of conventional latex agglutination immunoassay. The inventors found that use of larger size of latex particles with their diameter greater than 300 nm and use of higher coupling ratio of antibodies over available coupling sites and spaces on latex particles and as well as use of a right agglutination enhancer (stimulant) and proper heat stress treatment of the antibody coupled latex particles, a highly sensitive latex agglutination immunoassay for legumain can be developed with a limit of detection reached to <0.2 ng/mL. With the combination of the above mentioned improvements, the inventors developed the first latex agglutination based immunoassay for determining blood levels of legumain. The assay is fully automated with clinical chemistry analyzers, and the total reaction time is <10 min, which is a much faster and convenient assay in comparison with the time consuming and cumbersome ELISA assay that takes more than 4 hours. Using the fully automated latex immunoassay for legumain, the inventors determined the clinical cut-off values used for assessing high risks of cancers, especially solid tumors such as breast cancer, colorectal cancer and stomach cancer.

Latex particles used to practice embodiments as provided herein will be evident to the worker familiar with the field of latex agglutination immunoassay. In general, such particles require the properties necessary to serve as a stable support for the desired antibody reagent for the assay and to undergo agglutination in the presence of a stimulant or enhancer sufficient for analytical purposes. Latex particles are prepared generally by emulsion polymerization or suspension polymerization [Bangs, L. B. (1984) Uniform Latex Particles, Seragen Diagnostics Inc., Indianapolis, Ind., USA]. Swollen emulsion polymerization can also be used [Ugelstad, J. et al (1980) Adv. Colloid and Interface Sci. 13:101-140]. A good selection of latex particles are commercially available. Polystyrene particles are particularly useful.

The density of the latex particles, without limitation, will vary generally between about 0.1 mg/mL and about 0.1 g/mL. Most latexes are composed of particles that are roughly microspherical, having diameters, without limitation, that vary between about 0.04 and about 1.2 microns.

The attachment of the antibody reagent to the latex particles is a matter of applying conventional techniques. In general, the attachment can be covalent or noncovalent. The antibody reagent can consist of whole antibodies, antibody fragments, polyfunctional antibody aggregates, and the like. Normally, whole antibody or IgG fragments such as Fab, Fab', or F(ab')2 are employed. The antibody reagent can be derived by any available technique such as conventional antiserum and monoclonal techniques. However, the selection of the latex particle size, surface density of functional group or parking area and the concentration of antibody conjugation are unique and specific for each analyte, and the optimization of these parameters and conditions determines the success or failure of a latex immunoassay development.

The immunoassay reaction is conducted at a pH of 7.5 or greater so as to neutralize the positive character of legumain molecule which has a theoretic isoelectric point (IEP) of approximately 6.4, and thereby eliminate the nonspecific agglutination of the latex reagent in the presence of the blood sample. The pH of the reaction mixture will, of course, not be allowed to reach the IEP of legumain at which the immunoreactivity between the analyte and the latex reagent is substantially diminished, that is, to the point that a useful assay is no longer obtainable. Preferably, the pH of the aqueous reaction mixture will have a pH of between about 7.5 and about 10, preferably less than about 8.5, with a pH around 8.0 being particularly useful. Suitable buffers for this purpose can be selected on the basis of convenience and assay performance. Glycine and bicine buffers are preferred.

The immunoassay reaction as provided herein is conducted under the conditions that generate at least 50 delta mili O.D. between the background absorption and the absorption at 0.3 ng/ml of legumain in the sample, and at least 800 delta mili O.D. between the limit of quantitation (LOQ) and the highest point of the assay linearity.

Examples of the preparation of latex enhanced immunoassay reagents for determination of legumain in serum or plasma are provided in the Example section.

The following embodiments are intended to further describe and illustrate various aspects of the present disclosure, but not to limit, the scope of the present disclosure in any manner, shape, or form, either explicitly or implicitly.

Embodiment 1: A method for determination of blood levels of legumain molecule comprises:
1) mixing a serum or plasma sample containing or suspected of containing legumain molecule with a specific size or sizes of microparticles coated with antibody or antibodies against human legumain molecule or its degradation fragment(s);

2) measuring the optical or signal change of the reaction mixture, which is used to calculate the concentrations of legumain molecules in the sample by comparing the optical or signal change with calibrators of known concentrations of legumain;

3) comparing the concentrations of legumain in samples with the normal reference ranges or cut-off values, concentrations above the cut-off values are indications of higher risk of cancers.

Embodiment 2: The method according to the Embodiment 1, wherein the legumain molecule is of mammalian origin, preferably of human origin, and is an asparaginyl endopeptidase [EC 3.4.22. 34].

Embodiment 3: The method according to the Embodiment 1, wherein the antibodies are monoclonal or polyclonal antibodies having specific affinity towards mammalian legumain molecule, preferably towards human legumain molecule or its proteolytic degradation fragment(s).

Embodiment 4: The method according to Embodiment 1, wherein the microparticles are latex or gold particles, or magnetic particles of specific sizes (diameters) ranging from 40 to 400 nm. When magnetic particles are used, washing step(s) may be included in combination with chemiluminescence or fluorescence detection.

Embodiment 5: The method according to Embodiment 1, wherein the ratio of antibodies to the available coating sites on latex particles is between 0.5 to 1.0.

Embodiment 6: The method according to Embodiment 1, wherein the agglutination enhancer (stimulant) used is polyethylene glycol of molecular weight ranging from 600 to 100,000, and with a final concentration in R1 ranging from 0.3-1.5% (w/v).

Embodiment 7: The method according to Embodiment 1, wherein the agglutination enhancer (stimulant) used is polyvinyl pyrrolidone with a molecular weight from about 10,000 to about 750,000, and with a final concentration in R1 ranging from 0.1-3.0% (w/v).

Embodiment 8: The method according to the Embodiment 1, wherein the antibody coupled latex microparticles are heat stressed for at least 10 hours at a temperature between 30 and 50° C., preferably at 45° C. for 1-5 days.

Embodiment 9: The method according to the Embodiment 1, wherein the blood samples are serum or plasma from mammalian, preferably from human.

Embodiment 10: The method according to the Embodiment 1, wherein the cancers include breast cancer, ovarian cancer, colorectal cancer, stomach cancer, lung cancer and other types of solid tumors.

Embodiment 11: A kit for determination of blood levels of legumain molecules consists of at least two parts of reagents (R1 and R2), wherein one of the reagents contains microparticles coated with antibody or antibodies specifically against legumain molecules in the blood samples from mammalian, preferably from human, and the other reagent contains buffer with its pH values ranging from 3.0 to 10.0. A calibrator or a calibrator set is either included in the kit or is packed in a separated kit.

Embodiment 12: The method according to the Embodiment 7, wherein the blood sample is first mixed with the buffer followed by addition of the reagent containing the microparticles coated with antibody or antibodies specific for mammalian, preferably for human legumain molecule. The optical or signal change of the reaction mixture is measured, and the concentrations of legumain molecule in blood samples are determined using a calibration curve constructed by using a calibrator or calibrator set of known concentrations of legumain.

Embodiment 13: The method according to the Embodiment 8, wherein the concentrations of legumain in the samples are determined, and the risks of cancers, especially solid tumors including breast cancer, stomach cancer and colorectal cancer are assessed using the established cut-off values of 18.5±3 ng/mL for high risk of cancers including breast cancer, stomach cancer, colorectal cancer.

Embodiment 14: The method according to the Embodiment 9, wherein the preferred cut-off value for breast cancer, ovarian cancer, colon cancer, lung cancer and stomach cancer is 18.5 ng/mL for plasma or serum samples. A cut-off value can also be set between 15.0 ng/mL and 25.0 ng/mL according to sample conditions (female vs male) and type of cancers; whereas the preferred cut-off value for breast cancer and ovarian cancer is 18.5 ng/mL for plasma or serum samples, and a cut-off value can also be set between 10 ng/mL and 30/ng/mL for stomach cancer, colon cancer and lung cancer.

REFERENCES

Chen J. M., Dando P. M., Rawlings N. D., Brown M. A., Young N. E., Stevens R. A., Hewitt E., Watts C., Barrett A. J. Biol. Chem. 272:8090-8098, 1997.

Cheng Liu, Chengzao Sun, Haining Huang, Kim Janda, and Thomas Edgington. Cancer Res. 63, 2957-2964, 2003.

Gawenda J, et al. Breast Cancer Res Treat. 102(1): 1-6. 2007.

Guo P., Zhu Z., Sun Z., Wang Z., Zheng X., and Xu H. PLoS One. 8(9): e73090. 2013.

Half2003) Overexpression of legumain in tumors is significant for invasion/metastasis and a candidate en on S; Patel S; Vega F et al. FEBS Lett. 438 (1-2): 114-8. 1998.

Liu C, et al. (zymatic target for prodrug therapy. Cancer Res. 63(11): 2957-64.

Liu Y, Bajjuri K M, Liu C, Sinha S C. Mol Pharm. 1; 9(1):168-75. 2012.

Lin Y, Qiu Y, Xu C, Liu Q, Peng B, Kaufmann G F, Chen X, Lan B, Wei C, Lu D, Zhang Y, Guo Y, Lu Z, Jiang B, Edgington T S, Guo F. J Natl Cancer Inst. 106(4):dju012. 2014.

Liron Stern, Rotem Perry, Paula Ofek, Ariel Many, Doron Shabat, Ronit Satchi-Fainaro. Bioconjug. Chem. 20(3):500-10, 2009.

Mads H Haugen, Kjetil Boye, Jahn Martin Nesland, Solveig J Pettersen, Eivind Valen Egeland, Tripti Tamhane, Klaudia Brix, Gunhild M Maelandsmo, Kjersti Flatmark Eur. J. Cancer 51(1), 9-17, 2015.

Murthy R V, et al. (2005) Legumain expression in relation to clinicopathologic and biological variables in colorectal cancer. Clin Cancer Res. 11(6): 2293-9.

Schwarz G, et al. Biol Chem. 383(11): 1813-6. 2002.

Tanaka T, Inazawa J, Nakamura Y. Cytogenet Cell Genet. 74(1-2):120-3. 1996.

Wu M, Shao G R, Zhang F X, Wu W X, Xu P, and Ruan Z M. Asian Pac J Cancer Prev. 15(24):10773-7. 2014.

Yamane T, Murao S, Kato-Ose I, Kashima L, Yuguchi M, Kozuka M, Takeuchi K, Ogita H, Ohkubo I and Ariga H. Biochem. Biophys. Res. Commun. 438 (4), 613-618, 2013.

Ze Liu, Min Xiong, Junbo Gong, Yan Zhang, Nan Bai, Yunping Luo, Luyuan Li, Yuquan Wei, Yanhua Liu, Xiaoyue Tan & Rong Xiang. Nat Commun. 27; 5:4280. 2014.

EXAMPLE 1

Preparation of Reagents and Reaction Buffer Solutions

Preparation of Reagent 1 (R1):

As an example, the Reagent 1 (R1) buffer solution contains at least about the following amounts of chemicals per liter of solution:

| | |
|---|---|
| Tris base | 12.1 g |
| NaCl | 10 g |
| Sodium Thiocynate | 0.5 g |
| BSA | 2 g |
| Mouse gamma globulin | 0.05 g |
| Triton x-100 | 1 g |
| Glycerol | 5 g |
| $NaN_3$ | 0.9 g |
| 6N HCl/10M NaOH | pH 8.2 |

In this example, the final R1 reagent preparation is completed by addition of a certain amount (e.g., 0.5-1.5%) of PEG (6-100K), for example, as described below.

For 45 liter of R1 reagent, 324 g of PEG100K were added to make the final PEG100k of 0.72%. Amount of PEG100k=Liter of R1×optimum PEG100k concentration (%)×10 g/L=450×0.72=324 g. The calculated PEG100K was mixed well with the R1 buffer, and pH of R1 was adjusted to 8.2±0.1 with HCl and NaOH.

Preparation of Reagent 2 (R2)—Latex Particle-Antibody Conjugate:

1. In this example, 20 mM MES buffer with 100 mM NaCl, pH 7.3 was prepared as follows:

3.95 g MES, 1.844 g NaCl/liter $H_2O$, using 10 M NaOH or 6N HCl to adjust pH.

2. Preparation of legumain antibody is described below. Antibodies (800 mg, 3.9 mg/ml) from Abcam (ab125286 and ab47157, Abcam, Cambridge, Mass.) or antibodies from Santa Cruz Biotechnology (CA, US), such as sc-271312 and sc-133234, were dialyzed against 41 liter of MES buffer (prepared in step 1 above) in a dialysis tube (Spectrum), with two dialysis buffer exchange in a cold room for 2 days. Antibody concentration was measured using A280 with an extinction coefficient of 1.38.

Antibody Con. (mg/mL)=[$A280(0.135)$×diluent factor (31)]/1.38=3.05 mg/mL.

Preparation of Legumain wash buffer:

| | |
|---|---|
| Tris Base | 12.11 g, Tween 20 1.0 g in 1 liter H2O |
| 30 liter buffer: | 363.3 g Tris, 30 g Tween 20, 24 liter H2O, 170 mL 6NHCl, pH 8.2 |

Preparation of MES Activation buffer:

| | |
|---|---|
| MES | 3.905 g/L, for 30 liter, 117.15 g; 21 liter H2O |
| 6NHCl | 0 ml, 10M NaOH: ~30 mL; final pH 6.1 |

Preparation of legumain Reagent 2 (R2) diluent:

| | |
|---|---|
| Tris Base | 12.1 g/L |
| BSA | 2 g/L |
| Sodium Azide | 0.9 g/L |
| Sucrose | 120 g/L |
| Tween 20 | 0.1 g/L |
| HCL/NaOH | pH 8.2 |

Determination the amount of EDAC needed per liter of R2:

[µeq/g×batch size (L)×1.1%]/0.0052=[91×1000× 0.011]/0.0052=192500 ug=192.5 mg

For 10 times excess of EDAC: 192.5×10=1925 mg.

Determination of the optimum amount of IgG needed per liter of R2:

6/[(density (g/ml)×mean diameter µm]×2.5×10

6/(1.05×0.32)×2.5×10=446.4 mg

Determination of batch size of R2 (1.1% particle suspension) from IgG available:

Batch size=621.9 mg/446.4 mg=1.4 L R2 (1.1% particle suspension)

Particle Activation:

Add the calculated volume (0.154 L) of the original particle suspension stock (10.12%) and the MES Activation buffer of 1.25 L to a glass container and mix until homogenous.

Measure the initial aggregation ratio of the particle suspension by:

Blank a spectrophotometer with MES Activation buffer at 340 nm and 650 nm wavelengths. Dilute a small sample of particle suspension with the MES buffer so that it has an absorbance of 1.0+/−0.1 at 340 nm and record the dilution factor. Record the A340/A650 absorbance ratio as below:

Dilution factor 2.5 uL: 900 uL $A340/A650$=1.078/0.174=6.196

NHS and EDAC Activation:

Add the calculated amount of NHS (16.1 g) to the 1.1% particle suspension and mix for at least 10 min or until completely dissolved, but no more than 20 min. Using a stir plate to help dissolving (room temperature).

Add the calculated amount of EDAC (2695 mg) powder immediately to the particle suspension and mix vigorously at 2-8 C for 60 min+/−5 min using a stir plate (vigorous mixing should result in a visible vortex but without foaming).

Diafiltration and sonication of Activated particles:

Once the system is ready, start the diafiltration and collect the filtrate in an appropriate container. Adjust the follow rate of the incoming buffer so that the level of the liquid in the mixing vessel remains relatively constant. Turn the pump to a setting of 360 RMP or until inlet pressure reaches a maximum pressure of 10 PSI.

Turn on the sonicator to a setting of 30-50% of the maximum output.

Required amount of MES Activation buffer=12×batch size=1.2×1.4=17 L.

Diafilter and sonicate the particles until the required amount of MES activation buffer has been used. Continue to monitor the filtrate throughout the diafiltration process.

After the required amount of MES activation buffer has been used, take a small sample of the particles and measure the aggregation as previously described.

$A340/A650$=1.05/0.173=6.176

Take a small sample of the filtrate and measure the A280, make sure A280 is <0.1.

After the sonication is completed, disconnect the buffer line then continue diafiltration until the particle mixture is concentrated to approximately 50% of the original volume (before diafiltration volume).

Turn off the sonicator then drain the system.

Remove the mixing vessel containing the activated particles.

Antibody coupling to the activated particles:

Prepare the required amount of the activated particle in a glass mixing container capable of holding the combined volumes of the particles and IgG stock. Starting mixing the particle suspension at 2-8 C. Adjust the mixing speed so that a vortex is visible to ensure that adequate mixing is achieved.

Add the calculated amount of antibody (622 mg) to the activated microparticles (1.4 L) while mixing at room temperature. The coupling reaction is continued for 2 hours+/− 10 min.

Monitor the conjugation efficiency:

Take 500 uL of conjugation solution, centrifuge at 20K rpm for 20 min, (may centrifuge twice to remove the fine particles). Use the activation buffer to run the baseline spectrum (250-750 nm). Take 150-200 uL of the supernatant to record the spectrum. Read A280 and use the absorption and extinction coefficient of 1.38 to calculate the antibody concentration (mg/mL) in the supernatant. The coupling efficient=antibody concentration remaining in the supernatant/the total antibody concentration $A280=0.0276$; the supernatant antibody concentration=$A280/1.38=0.0276/1.38=0.02$ mg/mL The original total antibody concentration: 622 mg antibody in 1.4 L or 0.444 mg/mL.

The coupling efficiency=$(0.444-0.02)/0.444=0.955$ or 95.5%.

Glycine Blocking:

Required amount of 1M glycine solution=batch size× 0.1=1.4 L×0.1=0.14 L or 140 mL.

Add 140 mL of 1 M glycine solution to the particle suspension and continue mixing at 2-8 C for 6-24 hours.

Post Conjugation Aggregation Check:

Blank a spectrophotometer with the wash buffer at 340 nm and 650 nm. Dilute a small sample of particle suspension with the wash buffer so that it has an absorbance of 1.0+/− 0.1 at 340 nm. Read and record the A340/A650 absorbance ratio below and record the dilution factor:

$A340/A650=1.071/0.900=1.190$

Diafiltration and Sonication of Antibody Conjugated Microparticles:

Prepare a diafiltration and ultrasonic processor apparatus as described above.

Place the conjugated particles in an appropriate sealed mixing vessel. Turn on the pump to re-circulate the conjugated particles in the system. Ensure that there are no leaks in the system. Turn the pump to a setting up to 360 rpm or until the inlet pressure reaches a maximum pressure of 10 PSI.

Open the filtrate line to the hollow fiber module and monitor the filtrate. Ensure that the filtrate is clear and that the particles are not leaking through the filtrate.

Once the system is ready, start the diafiltration and collect the filtrate in an appropriate container. Adjust the flow rate of the incoming buffer so that the level of the liquid in the mixing vessel remains relatively constant.

Turn on the sonicator to a setting of 30-50% of maximum output.

Required amount of Wash Buffer=15×Batch Size=15× 1.4=21 L

Diafiltrate and sonicate the conjugated particles until the required amount of Wash Buffer is used. Continue to monitor the filtrate throughout the diafiltration process.

After the required amount of Wash Buffer has been used, take a small sample of the particles and measure the aggregation ratio as previously described using the Wash Buffer to blank. Record the results below:

$A340/A650=1.025/0.300=3.417$

Continue to sonicate until the target Aggregation value (∼6) is reached. Measure the final Aggregation result at the end of sonication and record the result below:

$A340/A650=1.045/0.169=6.183$

Turn off the sonicator then drain the system.

Remove the mixing vessel containing the conjugated particles.

Add BSA, sodium azide and sucrose to the conjugated particle suspension using the following calculations and amounts:

BSA: batch size×5 g/L=7.7×5=38.5 g

Sodium azide: batch size×0.9 g/L=7.7×0.9=6.93 g

Dissolve the above chemicals (BSA, sodium azide and sucrose) in small volume of wash buffer, and filtrate through a 0.45 um filter before addition to the conjugated particle suspension. Mix the conjugated particle well.

Check the pH of the suspension and adjust to 8.2+/−0.1 at room temperature with 1N HCl or 1M NaOH if necessary.

Heat Stress Treatment of Conjugated Microparticles:

Store the conjugated microparticles in a sealed container and place it into an incubator with temperature of around 40° C., preferably 45° C. for at least 1 day, preferably for 3-5 days+/−5 hours.

Final Aggregation and pH Check:

Check the aggregation ratio: $A340/A650=1.01/0.170=5.941$

R2 Microparticle Optimization:

Prepare different dilution of R2 microparticles by diluting with legumain R2 diluent, for example, to prepare a series dilution from 1:1.25 to 1:3 dilution, and check the background absorbance.

R1 Reagent Optimization by Adjusting % of PEG:

Prepare some legumain R1 reagent containing 0%, 1%, and 2% PEG

Adjust % PEG by dilution with 0% PEG R1 or adding 2% PEG R1

Using 3 different dilutions of R2 and 3 different concentrations of PEG in R1, to perform calibration curves on a chemistry analyzer.

Select the optimum % of PEG in R1 and optimum R2 dilution based on the background (Cal 0 activity), sensitivity (Cal 1 activity) and measuring range (Cal 6 activity–Cal 5 activity)/Cal 5 activity.

Select a combination of microparticle dilution and % of PEG in R1 which makes the calibration curve the best fit and widest window. For example, the optimum % PEG in R1 was found to be around 0.8%.

Prepare the bulk reagent R1 by adding the optimum % of PEG determined by above optimization experiments.

Prepare the bulk reagent R2 by making the optimum dilution of the conjugated latex particles with the legumain diluent according to the optimization results found from the above experiments.

Store both R1 and R2 reagents in 2-8° C. The shelf-life should be greater than 1 year from the manufacturing date.

Figure 1:
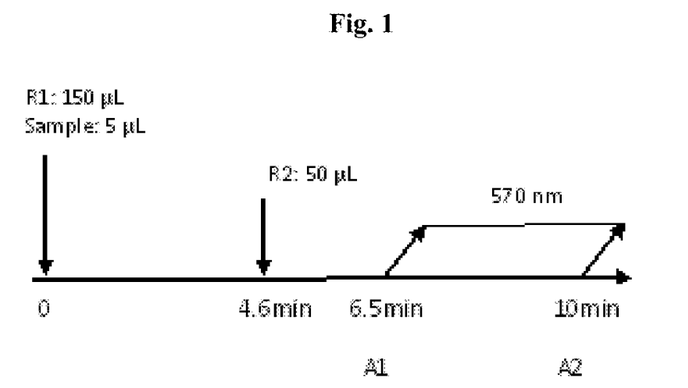
FIG. 1 illustrates the assay reaction procedure (parameter) on Hitachi 917 analyzer according to one aspect of the present disclosure.
Figure 2:
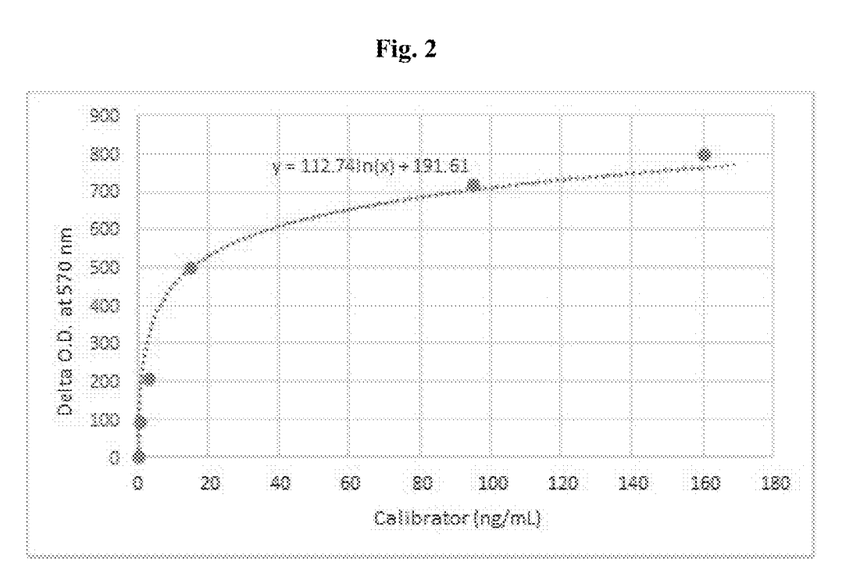
FIG. 2 illustrates an exemplary legumain latex enhanced immunoturbidimetric assay on Hitachi 917. A typical calibration curve is shown.

Using the optimized R1 and R2 reagents, the reaction procedures (FIG. 1) and optimized R1:R2 ratio (3:1) as well as the sample volume (3-5 μL), a typical dose response curve is shown in FIG. 2 of the drawing.

EXAMPLE 2

Calibration Curve

A typical calibration curve (dose response curve) of the latex enhanced legumain immunoassay (FIG. 2). The Cal activities (delta mAbs/min) are as follows when it is run on Hitachi 917 instrument with the primary wavelength set a 570 nm and the secondary wavelength set at 800 nm.

| Cal1 | 0 | 0.3 mAbs |
|---|---|---|
| Cal2 | 0.5 ng/mL | 95.1 mAbs |
| Cal3 | 3.0 ng/mL | 210.1 mAbs |
| Cal4 | 15.0 ng/mL | 500.3 mAbs |
| Cal5 | 95.0 ng/mL | 720.1 mAbs |
| Cal6 | 160 ng/mL | 800.2 mAbs |

Figure 3:
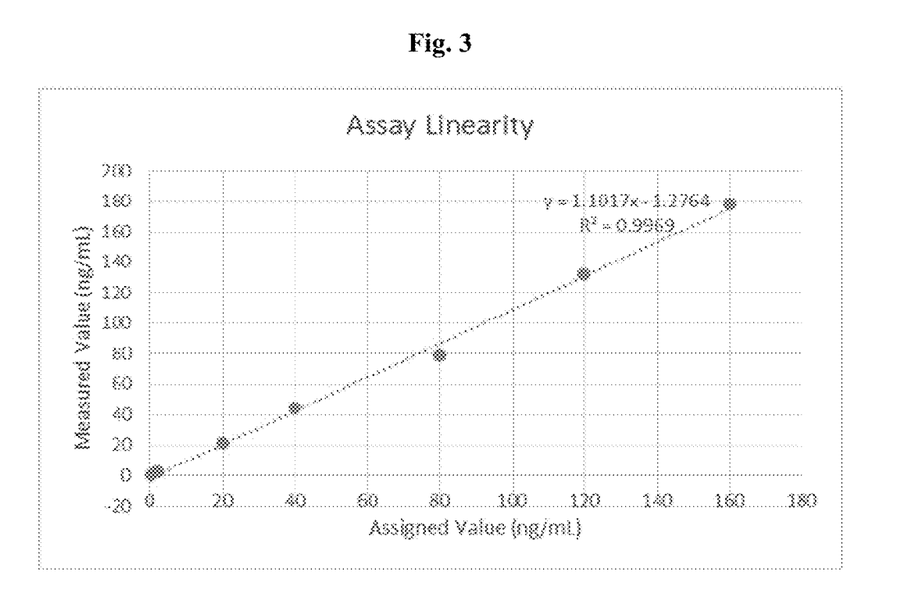
FIG. 3 illustrates an exemplary legumain latex enhanced immunoturbidimetric on modular P. A typical linearity curve is shown.

The latex enhanced legumain immunoassay was compared with a commercially available ELISA method, and the correlation of the test results of 65 samples were shown in FIG. 3. The assay had an r2 of greater than 0.98 in comparison with the predicate method.

Figure 4:
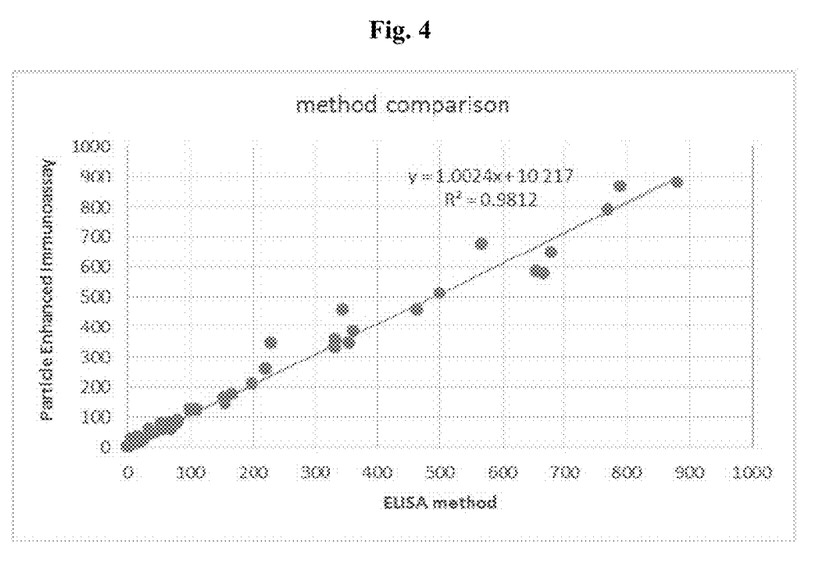
FIG. 4 illustrates an exemplary legumain method comparison (latex enhanced immunoturbidimetric vs. ELISA).

The latex enhanced legumain immunoassay had a wide assay dynamic range, and the assay linearity was examined to be in the range from 0.2 to 160 ng/mL as shown in FIG. 4 using a Roche Modular P analyzer. Samples with legumain values greater than 160 ng/mL need to be diluted with saline and re-tested. The results obtained need to be multiplied with the dilution factor.

EXAMPLE 3

Assay Results with Controls

Table 1. Assay Results with Controls: Controls of low, middle, and high values were tested using Hitachi 917 analyzer.

TABLE 1

Within Run Precision

| | Control 1 (0.5 ng/mL) | Control 2 (18.5 ng/mL) | Control 3 (110 ng/mL) |
|---|---|---|---|
| N | 80 | 80 | 80 |
| Mean | 0.492 | 18.38 | 112.30 |
| SD | 0.03 | 0.05 | 0.11 |
| CV % | 9.5 | 7.8 | 5.2 |

The precision of the Legumain Assay was evaluated according to Clinical Laboratory Standards Institute (formerly NCCLS) EP5-A guideline. In the study, three levels of Controls containing legumain were tested on Hitachi 917 two runs per day in duplicates over 20 working days.

EXAMPLE 4

Assay Results with Samples from Healthy Volunteer Breast Cancer Patients

Figure 5:
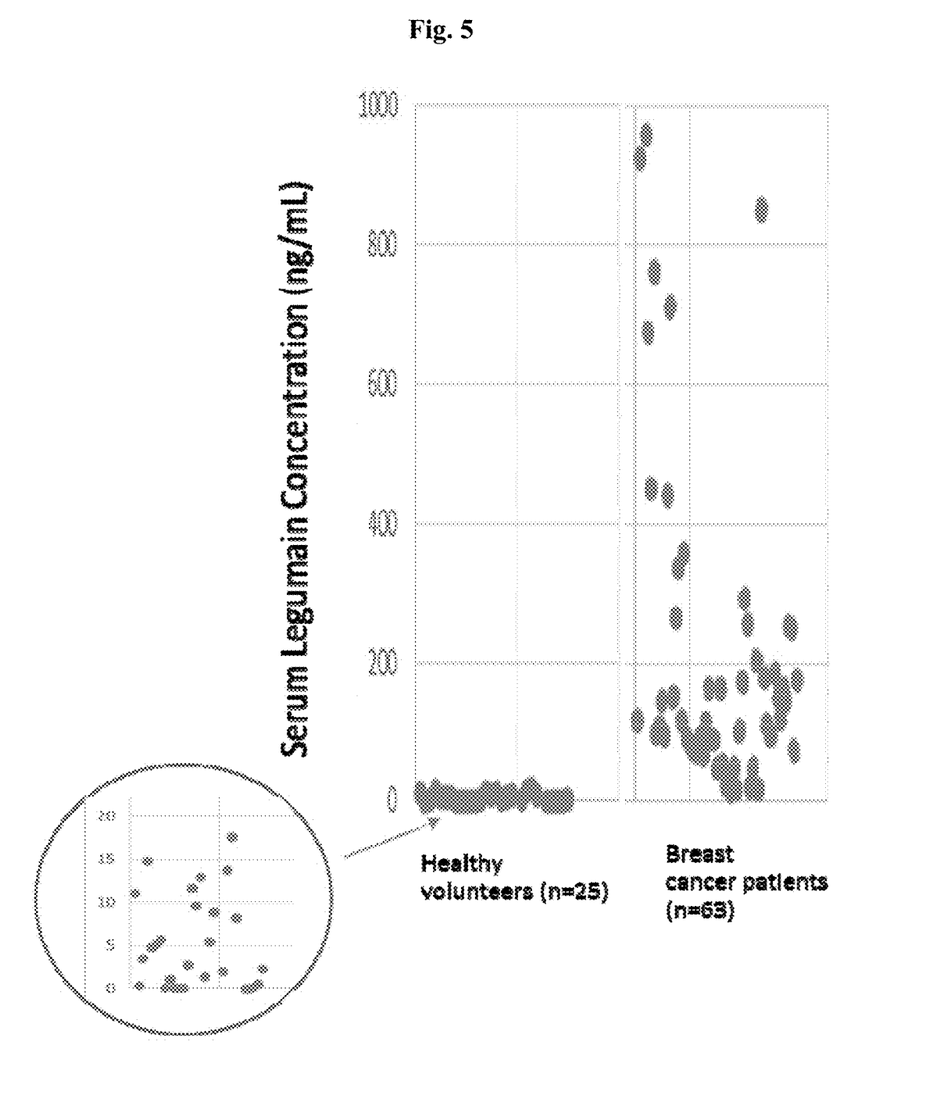
FIG. 5 illustrates exemplary legumain levels in blood from healthy volunteers and from breast cancer patients.

FIG. 5. Assay Results with Samples from Healthy Volunteer Breast Cancer Patients: Twenty five (25) serum samples from healthy volunteers and 63 serum samples from breast cancer patients were tested using the latex enhanced legumain immunoassay on Hitachi 917. The blood levels of legumain were ranging from 0 to 17.4 ng/mL for healthy volunteers, and the 99 percentile value of legumain concentration for healthy volunteers was at 15.7 ng/mL. In contrast, the legumain values of breast cancer patients were significantly higher than that of the healthy volunteer samples, it ranged from 18.5 to 958.0 ng/mL.

EXAMPLE 5

Assay Results with Samples from Stomach Cancer Patients

Figure 6:
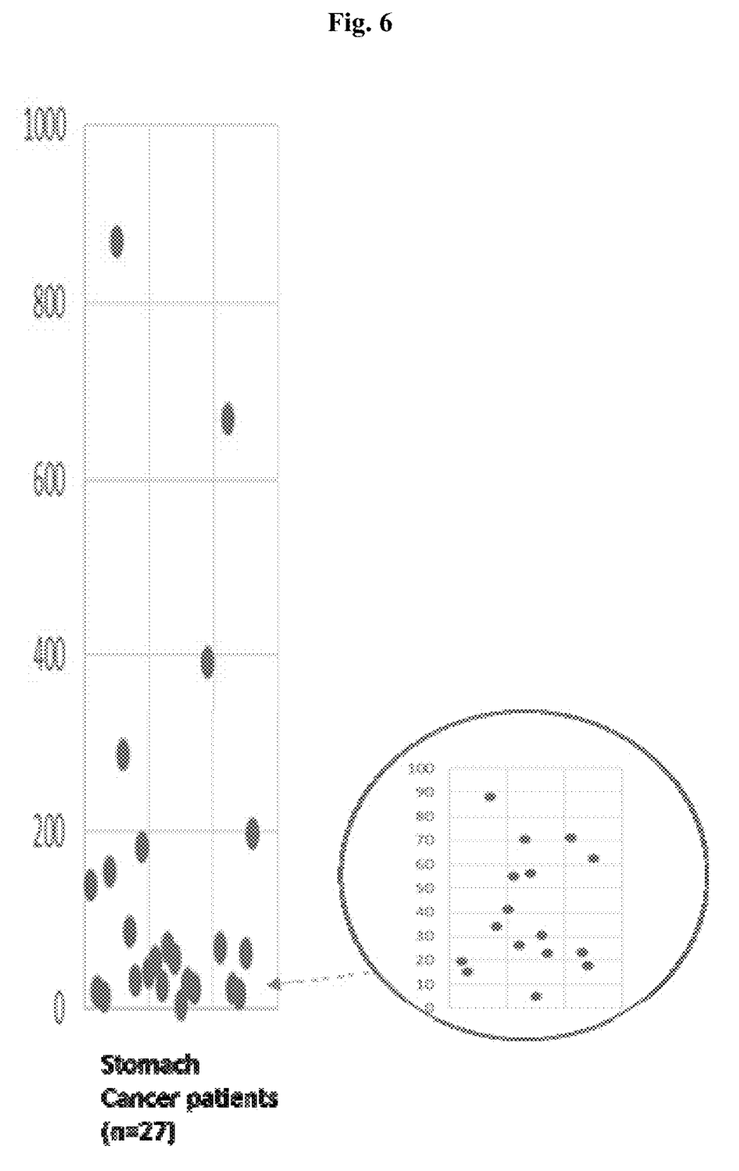
FIG. 6 illustrates exemplary legumain levels in blood from patients of stomach cancer.

FIG. 6. Assay Results with Samples from Stomach Cancer Patients: Twenty seven (27) serum samples from patients who were diagnosed of stomach cancer were tested using the latex enhanced legumain immunoassay using Hitachi 917 chemistry analyzer. The legumain levels in the serum from stomach cancer patients were found to range from 15.5 ng/mL to as high as 869 ng/mL except two samples that were below 11.0 ng/mL.

EXAMPLE 6

Assay Results with Samples from Colon Cancer Patients

Figure 7:
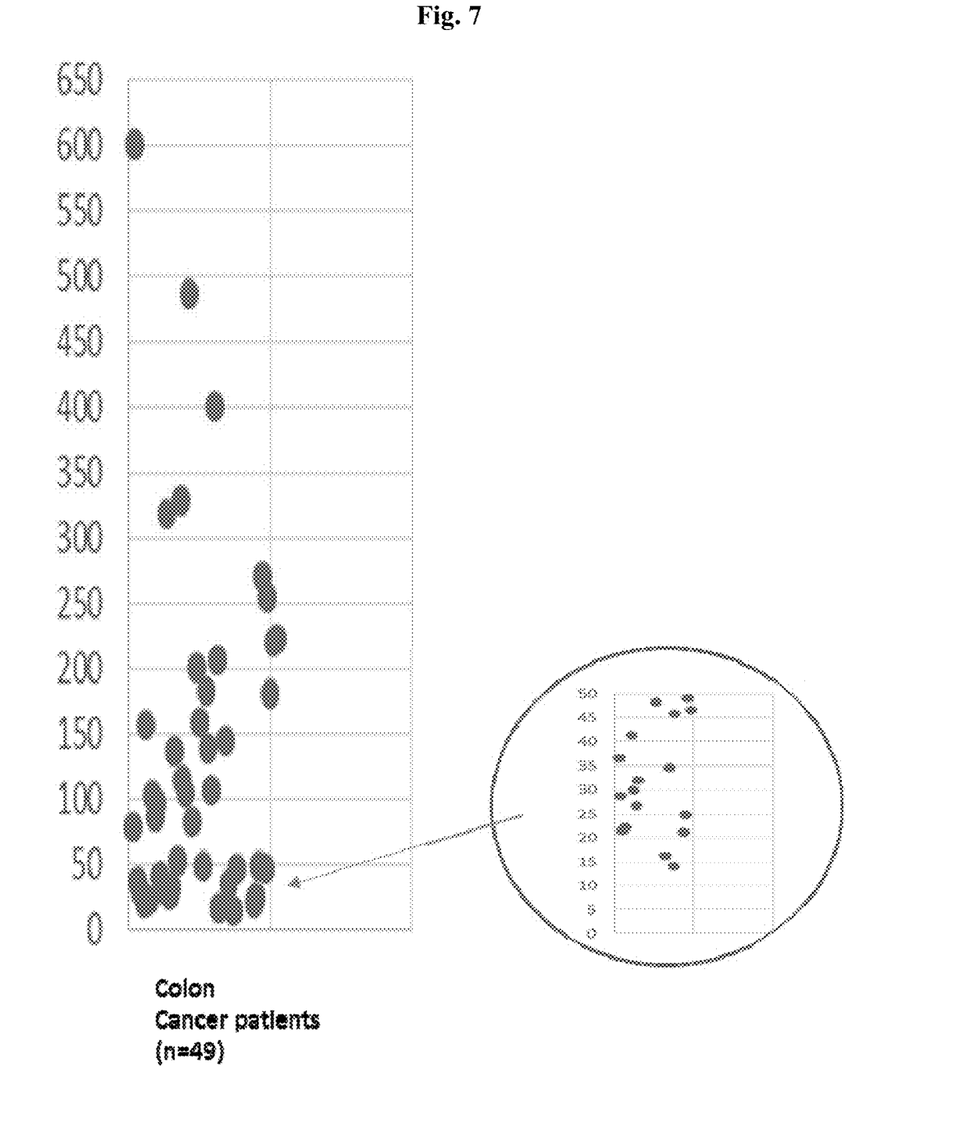
FIG. 7 illustrates exemplary legumain levels in blood from patients of colorectal cancer.

FIG. 7. Assay Results with Samples from Colon Cancer Patients: Forty nine (49) serum samples from patients who were diagnosed of colon cancer were tested using the latex enhanced legumain immunoassay on Hitachi 917 chemistry analyzer. The legumain levels in the serum of colon cancer patients were found to range from 21.2 ng/ml to as high as 601 ng/ml with two exceptional samples that were of values of 14.0 and 16.1 ng/mL.

What is claimed is:

1. A single-step method using heat-stressed microspherical latex microparticles in a legumain immunoassay for detecting legumain concentration in a blood, serum or plasma sample containing or suspected of containing legumain at concentrations as low as 0.2 ng per ml, comprising:
    (a) contacting the blood, serum or plasma sample with a plurality of microspherical latex microparticles,
    wherein the diameter of each of the plurality of microspherical latex microparticles is between 5 nm and 2 µm,
    and the plurality of microspherical latex microparticles is made by a method comprising:
      (i) coating each of the plurality of microspherical latex microparticles with an antibody or an antigen binding fragment thereof that specifically binds the legumain or a legumain fragment thereof,
      and the amount of antibody or the antigen binding fragment thereof attached to each of the plurality of microspherical latex microparticles is in amount wherein a ratio of the antibody or the antigen binding fragment thereof to available coating sites on each of the plurality of microspherical latex microparticles is between 0.1 and 1.0, and
      (ii) heat stressing the microparticle coated with the antibody or antigen binding fragment thereof for between 10 hours and 5 days at a temperature of between 30° C. to 50° C.,
    wherein the contacting further comprises an agglutination enhancer or stimulant comprising a polyethylene glycol having a molecular weight in a range of 600 Da to 100,000 Da at a final concentration of between 0.3 to 1.5% (w/v);
    (b) detecting the optical or signal change of the blood, serum or plasma sample contacted with the plurality of microparticles; and
    (c) determining the level of legumain and the legumain fragment in the blood, serum or plasma sample using a calibration curve and comparing the optical or signal change with a calibrator or a calibrator set of a predetermined levels of legumain, wherein the calibration curve is constructed by using a calibrator or calibrator set of predetermined concentrations of legumain,
wherein the sensitivity of the latex enhanced legumain immunoassay is between 0.2 to 160 ng/ml legumain.

2. The method of claim 1, wherein: the ratio of the antibody or antigen binding fragment thereof to the available coating sites on the microparticle is between 0.5 and 1.0.

3. The method of claim 1, wherein the diameter of the microspherical latex microparticle is between 10 nm and 500 nm.

4. The method of claim 1, further comprising: a step (d), comparing the level of legumain in the sample with a normal reference range or a cut-off value.

5. The method of claim 1, wherein the legumain is of mammalian origin.

6. The method of claim 5, wherein the legumain is of human origin.

7. The method of claim 1, wherein the legumain is an asparaginyl endopeptidase, or the legumain has an asparaginyl endopeptidase activity.

8. The method of claim 1, wherein the antibody or antigen binding fragment thereof is recombinantly produced or is a monoclonal or polyclonal antibody.

9. The method of claim 1, wherein the microspherical latex microparticle has a diameter ranging from 40 nm to 400 nm.

10. The method of claim 1, wherein an agglutination enhancer or stimulant is used in the contacting step.

11. The method of claim 10, wherein the molecular weight of the polyethylene glycol ranges from 600 Da to 50,000 Da.

12. The method of claim 1, wherein the microparticle coated with the antibody or antigen binding fragment thereof is heat stressed at 45° C. for one day and five days.

13. The method of claim 1, wherein the sample comprises a serum or plasma sample from a human, or a non-human mammal.

14. The method of claim 1, wherein the plurality of microspherical latex microparticles have embedded within a magnetic particle or plurality of magnetic particles.

15. The method of claim 1, wherein the antibody or antigen binding fragment thereof is specific for a mammalian legumain, a human legumain, or a mammalian legumain, a human legumain fragment.

16. The method of claim 1, wherein the antigen binding fragment is an Fab, $F(ab')_2$, Fv, or scFv.

* * * * *